United States Patent [19]

Carson et al.

[11] Patent Number: 4,469,659

[45] Date of Patent: Sep. 4, 1984

[54] SAMPLING DEVICE FOR BLOOD OXYGENATOR

[75] Inventors: Gary A. Carson, Evergreen; Roger J. Elgas, Littleton, both of Colo.

[73] Assignee: Cobe Laboratories, Inc., Lakewood, Colo.

[21] Appl. No.: 371,974

[22] Filed: Apr. 26, 1982

[51] Int. Cl.³ .............................................. A61M 1/03
[52] U.S. Cl. ...................................... 422/46; 422/45; 422/48; 435/2
[58] Field of Search ....................... 422/44, 45, 46, 48, 422/119; 128/DIG. 3; 435/2

[56] References Cited

U.S. PATENT DOCUMENTS

| 3,332,746 | 7/1967 | Claff et al. | 422/48 X |
| 3,396,849 | 8/1968 | Lande et al. | 422/48 X |
| 3,468,631 | 10/1969 | Raible et al. | 23/258.5 |
| 3,480,401 | 11/1969 | Holm et al. | 422/48 |
| 3,579,810 | 5/1971 | Mon et al. | 422/45 X |
| 3,907,504 | 9/1975 | Hammond et al. | 422/46 |
| 3,927,980 | 12/1975 | Leonard | 435/2 X |
| 3,998,593 | 12/1976 | Yoshida et al. | 422/46 |
| 4,127,111 | 11/1978 | Drolet | 422/44 X |
| 4,197,876 | 4/1980 | Lobdell | 137/625.47 |
| 4,237,091 | 12/1980 | Lobdell | 422/46 |

FOREIGN PATENT DOCUMENTS

| 2343845 | 3/1974 | Fed. Rep. of Germany | 422/48 |
| 1437493 | 5/1976 | United Kingdom | 422/48 |
| 279896 | 5/1977 | U.S.S.R. | 422/46 |

Primary Examiner—Barry S. Richman

[57] ABSTRACT

Blood oxygenating apparatus having a sampling access device connected to the blood outlet port and a blood inlet port of the apparatus by a sample supply line and return line and means to cause the pressure at the blood outlet port to be sufficient to cause a small continuous flow of blood through the lines and access device.

5 Claims, 9 Drawing Figures

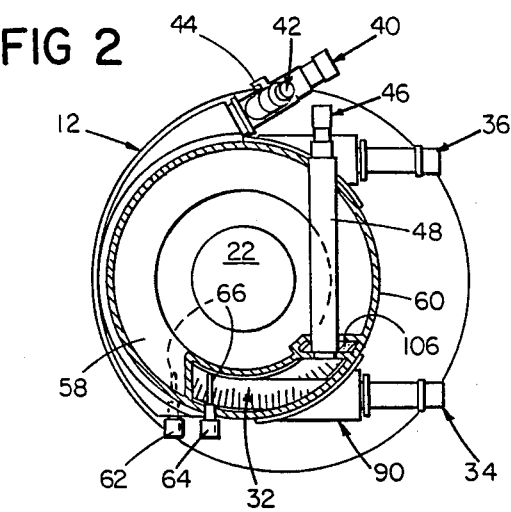
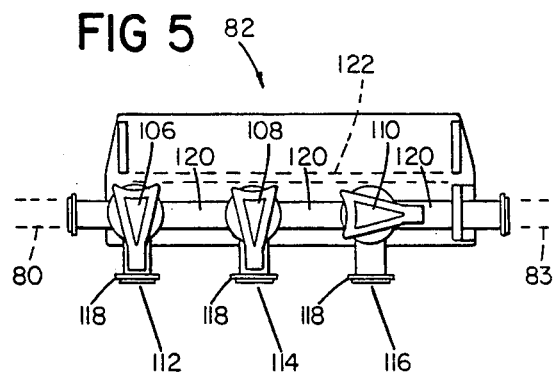
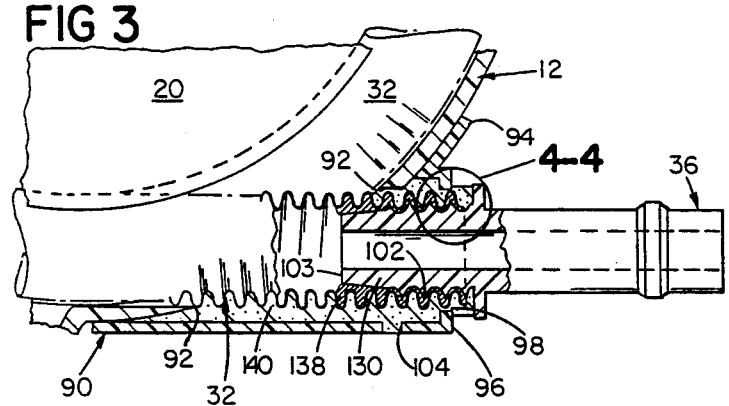
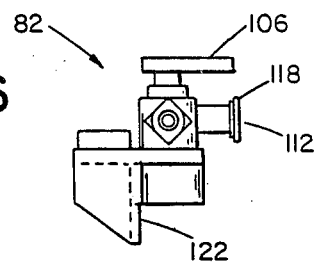
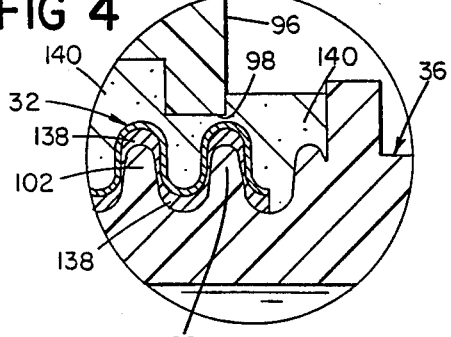
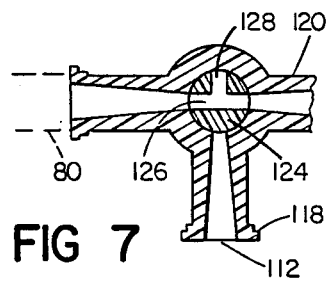
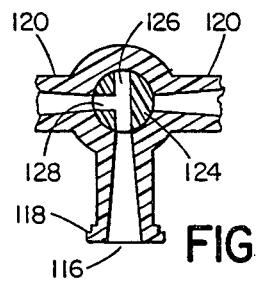
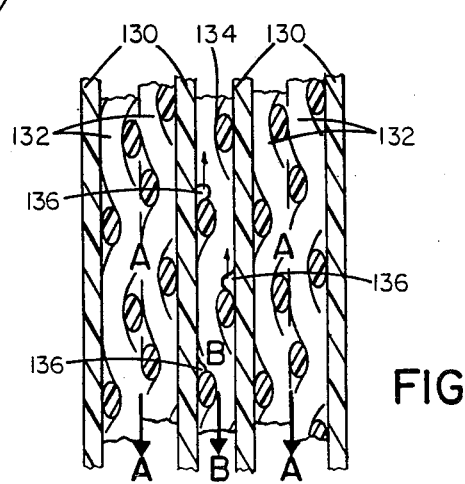

4,469,659

SAMPLING DEVICE FOR BLOOD OXYGENATOR

FIELD OF THE INVENTION

The invention relates to blood oxygenating apparatus.

BACKGROUND OF THE INVENTION

It is often desirable to take samples of oxygenated and unoxygenated blood during oxygenation to measure oxygen concentration and other parameters. Samples are typically removed by connecting a syringe to a sample port, and removing a sample of blood.

SUMMARY OF THE INVENTION

In general the invention features connecting a sampling access device to the blood outlet port and a blood inlet port of the oxygenator by a sample supply line and a sample return line and providing means to cause the pressure at the blood outlet port to be sufficient to cause a small continuous flow of blood through the lines and access device. Because of the continuous flow, clotting is avoided, and representative samples are guaranteed. Unsampled blood is not wasted but is returned via the return line to the oxygenator. Air bubbles accidentally injected into the sampling access device will be carried to the oxygenator, which includes means to remove them from the blood. This is because flow to the blood outlet port, where the bubbles would be introduced into a patient's bloodstream, is severely restrained by the continuous flow in the other direction, the distance from the access device to the blood outlet, and the increased pressure at the blood outlet.

In preferred embodiments the means for removing air bubbles includes a blood storage reservoir device, and most preferably it also includes a membrane type fluid flow transfer device having blood flowing downward between microporous membranes; the supply and return lines are flexible to permit moving of the access device to a convenient sampling location; detachable mounting means for the access device are provided on a housing of the blood oxygenator; and the return line is connected to a blood inlet port of the oxygenator for receiving venous blood from a patient and the access device has more than one portal and means to block flow through said device to permit removal of unoxygenated samples from said blood inlet.

PREFERRED EMBODIMENT

The structure, construction and operation of the presently preferred embodiment of the invention will now be described, after first briefly describing the drawings.

DRAWINGS

FIG. 2 is a horizontal sectional view, taken at 2—2 of FIG. 1, of the FIG. 1 apparatus.

FIG. 3 is a horizontal sectional view, taken at 3—3 of FIG. 1, of a plastic fitting and its connection to said oxygenating apparatus.

FIG. 4 is an enlarged, diagrammatic portion of the FIG. 3 view indicated at 4—4.

FIG. 5 is a plan view of a sampling access device of the FIG. 1 apparatus.

FIG. 6 is a side elevation of the FIG. 5 device.

FIGS. 7 and 8 are schematic representations of sampling valves of the FIG. 5 sampling access device in different positions.

FIG. 9 is a diagrammatic vertical sectional view of an internal portion of a membrane device of the FIG. 1 apparatus.

STRUCTURE

Figure 1:
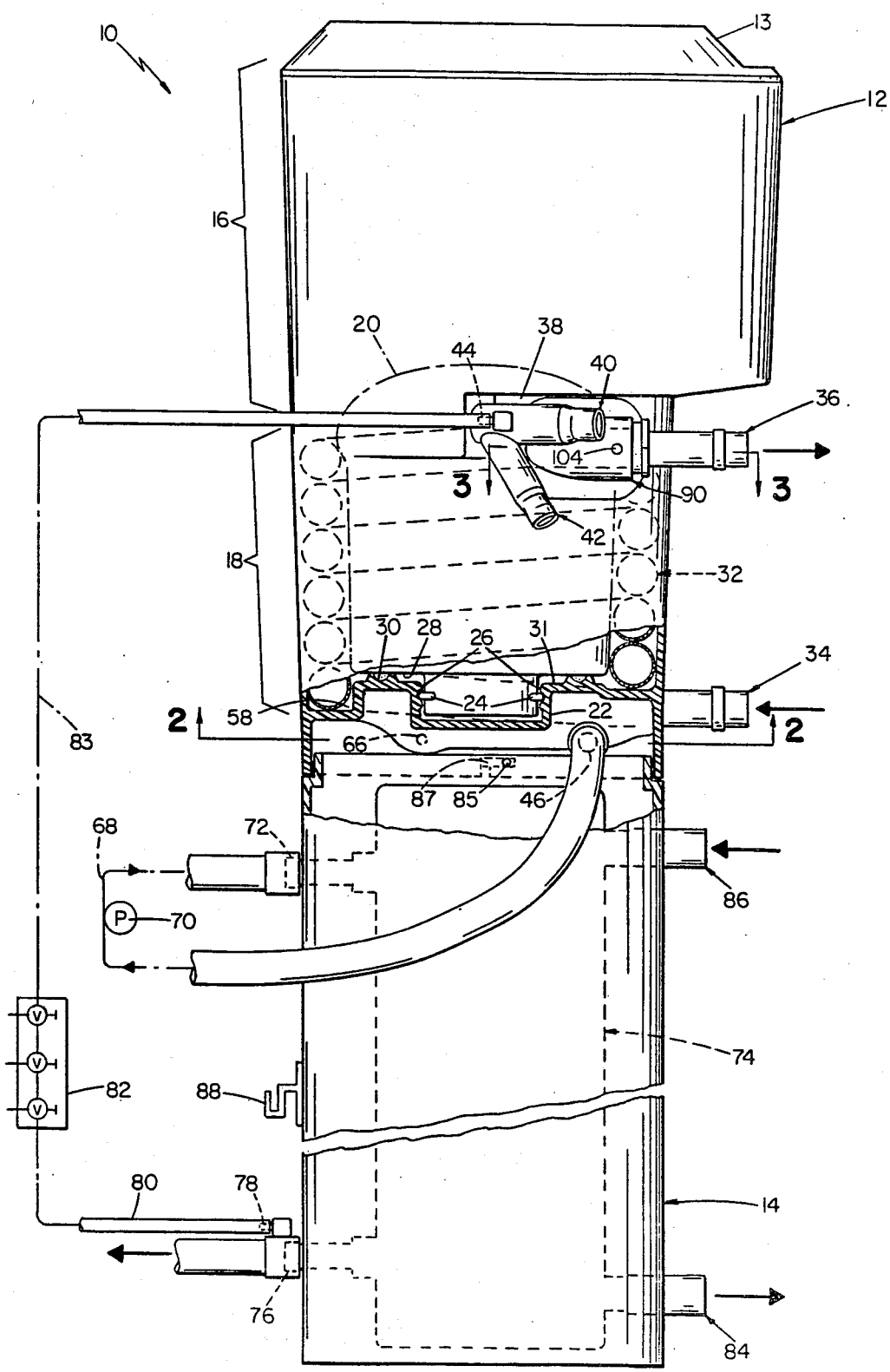
FIG. 1 is an elevation, somewhat diagrammatic and broken away, of blood oxygenating apparatus according to the invention.

Referring to FIG. 1 there is shown blood oxygenating apparatus 10 having upper molded polycarbonate casing 12, cap 13 and lower molded plastic support base 14. The portion of casing 12 designated 16 partially defines a blood reservoir storage region, and it is located on top of a portion 18 encasing the blood heating components. In the center of the blood heater is white molded-plastic central support member 20, which is connected to the bottom 22 of plastic casing 12 by threads 24 that interfere with protrusions 26 on casing 12. Polyurethane potting between the lower surface 28 of support member 20 and the upward facing annular groove 30 on lower horizontal portion 31 of casing 12 provides a seal between member 20 and casing 12.

Helically corrugated tube 32 is wound between central support 20 and housing 12. The tubing is made of stainless steel, is available from the Flexonics Division of UOP, Inc., Bartlett, Ill. as part no. 460L, is ultrasonically degreased before construction and has a pitch of approximately 0.134 inch, an exterior thread depth of about ⅛ inch and an external diameter of approximately ¾ inch. The tubing makes 5½ revolutions around member 20, and there is a small clearance between tubing 32, member 20 and casing 12. One end of tube 32 is sealably connected to plastic heated water inlet fitting 34, and the other end is similarly connected to identical heated water outlet fitting 36. Blood inlet 38 has port 40 for connection to a supply line of venous blood from the patient, port 42 for blood obtained from the patient's chest during surgery, and smaller return port 44 for connection to return line 83 of a sampling system, discussed in detail below. Blood inlet 38 enters casing 12 at a location just above the upper surface of the top winding of tube 32. At the bottom of heating portion 18 is blood outlet port 46, which is connected by tube 48 (FIG. 2) to the lowermost point of channel 58, which contains the lowermost winding of helically corrugated tube 32. Channel 58 is at its deepest near heated water inlet fitting 34; it gradually becomes more shallow as it extends clockwise (FIG. 2) around the circumference of the lower portion of plastic casing 12, and ends above the junction of tube 48 with its deepest portion. The shallow end of channel 58 is approximately even with the lower portion of center member 20.

Referring to FIG. 2, sockets 62, 64 (of the type disclosed in U.S. Pat. No. 4,237,091) for temperature probes are provided in heating portion 18. Socket 64 is in a recess in channel 58 below tube 32 located just upstream of the junction of tube 48 and channel 58. Socket 62 is located about ⅛ inch above the highest winding of heat exchanger tube 32. Both of these sockets are located on the opposite side of casing 12 from the side shown in FIG. 1. They have hollow plastic fittings extending out from the plastic casing 12, and hollow heat conducting portions 66 extending into the blood chamber within casing 12 at the top and bottom of heating portion 18. Thus, temperature probes (not shown) inserted into fittings 62, 64 will be isolated from the blood but in a heat conducting relationship with it.

Referring to FIG. 1, blood outlet 46 is connected by tube 68 to peristaltic pump 70 and blood inlet port 72 of membrane type fluid flow transfer device 74 (which is described in detail in a U.S. patent application entitled "Potting Seal For A Fluid Flow Transfer Device", filed simultaneously with this application by Roger J. Elgas and Gary A. Carson). Device 74 also has blood outlet port 76 for connection to a blood return line to the patient. Sample line port 78, for connection to sample tube 80 and sampling access device 82, described in detail below, is also connected to the blood return port 76. Within device 74 is a pleated semipermeable membrane (available from Celanese, Summit, N.J. under the trade designation Celgard 2402), a microporous sheet made of polypropylene with 0.2 by 0.02 micron holes. Microporous membranes suitable for use in transfer device 74 have pores sized large enough to allow air to pass through them at a higher rate than that of the slow molecular diffusion of homogeneous membranes, but small enough to prevent the flow of blood through them to the air channels at the transmembrane pressures achieved in the devices. The fold edges of the pleated sheet are potted to the housing of the device, and spacers are placed between adjacent folds. The pleated membrane defines alternate blood passages communicating with ports 72 and 76 and air passages communicating with air inlet port 86 and air outlet port 84. Device 74 is removably mounted within support base 14. On the side of base 14 is clip 88 to provide mounting for sampling device 82 when it is not detached from base 14.

Base 14 has a pair of protuberances 85 (one on each side), extending outwardly from the side wall near its top for mating with corresponding L-shaped slots 87 in casing 12 at its bottom.

Referring to FIGS. 3 and 4, there is shown the sealable connections of fitting 36 and the end of tube 32 to each other and to housing 12. The end of tubing 32 extends through elliptical hole 92 in plastic casing 12. Tube cover seal 90 has a flange portion 94 completely surrounding hole 92 and extending portion 96 with circular hole 98 in its end. Plastic fitting 36 has external threads 102 formed on its interior end, generally conforming to the shape of, and providing a small clearance with, the interior surface of tube 32 to provide secure engagement between the tube and fitting. Fitting 36 also has nonthreaded extension 130 with a diameter smaller than the internal diameter of tube 32. Potting material 138 occupies the regions between the threads of fitting 36 and the interior surface of tube 32. Tube cover seal 90 is adhered to casing 12, and a liquid-tight seal is formed between the end of tube 32, casing 12, tube cover seal 90 and fitting 36 by polyurethane potting 140. Plastic fitting 34 is similarly connected to casing 12 near its bottom and to the other end of tube 32.

Referring to FIGS. 5 through 8, sampling access device 82 is shown connected to sample supply line 80 and return line 83 (in phantom). Three color-coded valve knobs 106, 108, 110 are shown with their associated sample ports 112, 114, 116, each having projections 118 for mating with teeth on sampling connectors (not shown). The three valves are connected in series between lines 80 and 83 by tubes 120. A vertical tab 122 mates with clip 88 when sampler 82 is mounted on the side of base 14. Valve knobs 106, 108 are in the nonsampling position, permitting flow of liquid from tube 80 through tubes 120. (FIG. 7 shows the corresponding orientation of rotatable flow director 124—connected to knob 106 or 108—with passage 126 directing flow between tubes 120, and transverse passage 128 being blocked.) Valve knob 110 is in one sampling position, diverting all flow from supply line 80 to sample pot 116. (FIG. 8 shows the corresponding orientation of rotatable flow director 124 with passage 128 and 126 diverting flow to sample port 116 and blocking flow to downstream tube 120 and return line 83.) Another sampling position is with director in the position 180° from that in FIG. 7.

Referring to FIG. 9, portions of adjacent air channels A and blood channel B are shown separated by pleated membrane 130. Spacers 132, 134 in channels A, B, respectively, space adjacent folds of membrane 130. Air bubbles 136 in blood channel B are shown adjacent to the center folds of membrane 130. The upward pointing arrow indicates the direction of the buoyancy force owing to the different densities of air and blood; the downward pointing arrow indicates the direction of travel of blood and air in the channels.

CONSTRUCTION

In constructing device 10 the blood heating components must be assembled within casing 12. First tube 32 is wound around central support member 20. Member 20 and tube 32 are then inserted into the heating portion 18 of housing 12, and member 20 is rotated so that threads 24 lock with projections 26, and the annular projections defining annular groove 30 contact surface 28. Potting is thereafter injected into groove 30 through holes (not shown) in horizontal portion 31 to seal member 20 to casing 12. The ends of tube 32 are pulled through holes 92 and sealed to fittings 34, 36 and casing 12. Adhesive is applied to the inner surface of flange 94 and corresponding areas of housing 12 around hole 92. Tube seal 90 is then placed against the outer wall of housing 12 with the end of tube 32 extending slightly from or being flush with hole 98. Potting is then applied to the exterior surfaces of threads 102, and fitting 36 is mated with tube 32. Smaller diameter extension 103 facilitates insertion and threading of fitting 36 with tube 32 and avoids blockage of the fitting's flow path by potting squeezed out from the threads. Additional potting is then injected through hole 104 (FIG. 1), which is covered by a tape during construction, into the regions between tube cover seal 90 and the exterior surface of tube 32 and wall 12. After the potting has cured, the tape is removed. Fitting 34 and its corresponding tube seal 90 is sealed to housing 12 in a similar manner. Temperature probe sockets 62, 64 are adhesively mounted in holes in casing 12. Tube 48 is inserted into a hole communicating with channel 58, and potting is poured into recess 106 (FIG. 2) to provide a seal. The valves in sampler 82 are constructed in a manner similar to that disclosed in U.S. Pat. No. 4,197,876, and the construction of membrane device 74 is described in the above-mentioned patent application.

OPERATION

To begin oxygenation, venous blood from a catheter or other source is supplied to the oxygenating apparatus through blood intake port 40 at a rate of approximately 5 to 6 liters per minute. The blood enters reservoir portion 16 and flows between the corrugations of heat exchanging tube 32 and casing 12 and member 20 in the heating portion 18. If the level of blood drops below the top of white central member 20, it becomes visible and provides a warning that the level is below a desired level. From heating portion 18 the blood is pumped by pump 70 into membrane device 74. (At the beginning, the blood may be recycled to the blood inlet to remove bubbles initially introduced into or formed within the apparatus.) A mixture of compressed air and oxygen is supplied to air port 86 of device 74 so that the pressure of the air within the membrane device is approximately 5 mm Hg above atmospheric pressure. The blood is pumped to result in a midline (there is a drop in pressure from the blood inlet to the blood outlet) blood pressure within device 74 of approximately 150 mm Hg above the pressure of air. Because the partial pressure of oxygen in the gas mixture is higher than that in the blood, oxygen will pass through the microporous membrane and become dissolved in the blood even though the blood pressure is higher than the air pressure. Because the blood flows downward through device 74, air bubbles that are accidentally introduced into it, e.g., bubbles 136 in FIG. 9, are generally detained near the top by buoyancy and are inhibited in their downward travel by spacer strands. Bubbles that do travel, do so at a slower velocity than that of the blood and have an increased residence time in the blood channel B. In any event, all air bubbles pass through the pores of the membrane to the gas side of the membrane, and introduction of gas bubbles into the patient's bloodstream is prevented. This removal of air bubbles from the blood results from maintaining the blood at a higher pressure than the air, using a microporous membrane, and employing the increased residence time provided by the spacer strands and the downflowing blood and upward directed buoyancy forces on the bubbles. The rate of passage of air bubbles through the membrane depends, in addition to these factors, on the blood surface tension, which depends upon the makeup of the blood, e.g., the concentration of red blood cells. Also, because the blood reservoir portion 16 is located above the membrane device 74, and the device is constructed as an integral unit, potential gas siphoning problems such as those that are caused when the blood reservoir is at a lower elevation than the membrane device during nonuse do not occur.

Oxygenated blood continuously flows through small diameter supply tube 80, sampler 82, and return line 83 at approximately 50 to 100 cc/min (compared with 5 to 6 liters per minute for the flow through the oxygenating apparatus 10) owing to the increased pressure at outlet port 76 caused by pump 70, and samples can be removed from access ports 112, 114, 116 on sampling device 82. Samples of oxygenated blood are supplied under pressure when any of the valves knobs are rotated to the position of knob 110, or when a knob is pointed away from its access port so that director 124 is 180° from its position in FIG. 7. If a sample of unoxygenated blood from blood inlet 38 is desired, the flow through line 80 must be blocked, and line 83 (approximately 15 cc in volume) flushed with unoxygenated blood prior to removing a sample. This can be done by connecting a syringe to port 114, turning its obstructor to a position 180° from that shown in FIG. 8 (thereby blocking flow from line 80), removing the oxygenated blood from line 83 with the syringe, turning the obstructor for valve 116 to the same position, and removing the unoxygenated sample from port 116. The blood pulled into the syringe to flush line 83 before sample removal can then be returned to the system. Because of the continuous flow through tube 80, clotting is avoided, and representative samples are guaranteed. Unsampled blood is not wasted but is returned via tube 83 to blood return port 44 and the blood reservoir in casing 12. Any air bubbles accidentally injected into the sampling system at sampling access device 82 are carried to the reservoir and removed from the blood. This is because flow to the outlet port 76, where the bubbles would be carried with the blood to a patient's bloodstream, is severely restrained by the continuous flow in tube 80 in the other direction, the distance from the sampler 82 to outlet port 76, and the increased pressure at port 76 relative to that at sampling device 82. Also, because tubes 80, 83 are flexible and long, sampling device 82 can be detached from clip 88 and moved to a convenient sampling location.

OTHER EMBODIMENTS

Other embodiments will be apparent to those in the art. For example, blood inlet port 38 could be connected near the top of casing 12 or to cap 13.

Also, a blood defoamer could be placed in the reservoir storage region in portion 16 to facilitate removal of bubbles introduced into the oxygenator.

OTHER INVENTIONS

Subject matter relating to the integral oxygenator construction was the joint invention of Gary A. Carson, Roger J. Elgas and Timothy M. Gordon, whose U.S. patent application Ser. No. 372,065, entitled "Integral Blood Oxygenator", filed Apr. 26, 1982.

Subject matter relating to the oxygenator with downward flow past a microporous membrane was the joint invention of Roger J. Elgas and Timothy M. Gordon, whose U.S. patent application Ser. No. 371,973, entitled "Blood Oxygenator", filed Apr. 26, 1982.

Subject matter relating to the fitting for a heat exchanging tube was the joint invention of Timothy M. Gordon and Roger J. Elgas, whose U.S. patent application Ser. No. 371,979, entitled "Fitting for Corrugated Tube", filed Apr. 26, 1982.

We claim:

1. Blood oxygenating apparatus comprising
   means for continuously heating and oxygenating blood,
      said means including a blood inlet port, a blood outlet port for returning oxygenated blood to the patient via a patient return line, a mass transfer device, and means to remove air bubbles introduced into said blood inlet port,
   a sample supply line connected to said outlet port and having a diameter smaller than that of said patient return line and adapted to have a smaller flow through it than that through said patient return line,
   a sampling access device having an inlet connected to said sample supply line, a sampling port providing access for removal of blood flowing through said device, and an outlet port permitting continuous flow through said sampling device,
   a sample return line connected between said sampling device and said blood inlet port, and
   pumping means to cause the blood at said outlet port to have sufficient pressure to flow through said supply line, sampling device, and return line,
      said mass transfer device and said means to remove air bubbles including a membrane type fluid flow transfer device having an inflow port communicating with upper ends of channels defined by microporous membranes and an outlet port communicating with lower ends of said channels to result in downward flowing blood between microporous membranes within said membrane mass transfer device to detain bubbles introduced into said membrane device, and said pumping means maintaining the pressure on the blood side of said membranes sufficiently above that on said air side to cause substantially all accidentally introduced air bubbles to pass completely through said microporous membranes before being carried to the blood outlet port by the flow of blood.

2. The apparatus of claim 1 wherein said means to remove air bubbles includes a blood storage reservoir operatively connected to said blood inlet port and having a surface exposed to air.

3. The apparatus of claim 1 wherein said return line and said supply line are made of flexible tubing.

4. The apparatus of claim 3 wherein said means for continuously heating and oxygenating blood includes a housing with means for detachably mounting said sampling access device thereto.

5. Blood oxygenating apparatus comprising,
means for continuously heating and oxygenating blood,
said means including a blood inlet port, a blood outlet port for returning oxygenated blood to the patient via a patient return line, and means to remove air bubbles introduced into said blood inlet port,
said blood inlet port being a port for receiving venous blood from a patient,
a sample supply line connected to said blood outlet port and having a diameter smaller than that of said patient return line and adapted to have a smaller flow through it than that through said patient return line,
a sampling access device having an inlet connected to said sample supply line, a sampling port providing access for removal of blood flowing through said device, an outlet port permitting continuous flow through said sampling device,
a sample return line connected between said sampling device and said blood inlet port,
said sampling access device including valve means to block flow to said sampling port from said supply line to permit removal of samples from said blood inlet port through said sample return line,
said sample supply line, said sampling access device, and said sample return line comprising a single recirculation line between said outlet port and said inlet port, and
pumping means to cause the blood at said outlet port to have sufficient pressure to flow through said supply line, sampling device, and return line,
whereby samples of oxygenated blood can be removed from said blood flowing through said access device when said valve means is not activated, and samples of venous blood can be removed from said access device when said valve means is activated.

* * * * *

REEXAMINATION CERTIFICATE (3283rd)

United States Patent [19]
Carson et al.

[11] B1 4,469,659
[45] Certificate Issued Jul. 29, 1997

[54] SAMPLING DEVICE FOR BLOOD OXYGENATOR

[75] Inventors: Gary A. Carson, Evergreen; Roger J. Elgas, Littleton, both of Colo.

[73] Assignee: Cobe Laboratories, Inc., Lakewood, Colo.

Reexamination Request:
No. 90/004,465, Nov. 22, 1996

Reexamination Certificate for:
Patent No.: 4,469,659
Issued: Sep. 4, 1984
Appl. No.: 371,974
Filed: Apr. 26, 1982

[51] Int. Cl.$^6$ .......................... A61M 1/14; A61M 1/34; A61M 1/36
[52] U.S. Cl. ................... 422/46; 422/47; 422/48; 422/119; 604/4; 604/5
[58] Field of Search ................ 422/47, 48, 46, 422/119; 604/4, 5; 128/DIG. 3; 435/2

[56] References Cited

U.S. PATENT DOCUMENTS

| | | | |
|---|---|---|---|
| 3,794,468 | 2/1974 | Leonard | 422/46 |
| 3,989,626 | 11/1976 | Bentley | 422/46 |
| 4,205,042 | 5/1980 | Lobdell et al. | 422/46 |
| 4,256,692 | 3/1981 | Cover | 422/46 |

FOREIGN PATENT DOCUMENTS

| | | |
|---|---|---|
| 2452936 | 10/1980 | France. |
| 1437493 | 11/1976 | United Kingdom. |

OTHER PUBLICATIONS

Article, "A New Idea for Venting Arterial Line Filters", *The Journal If Extra-Corporeal Technology*, 1981.
Advertisement for Tygon Tubing: *The Journal of Extracorporeal Technology*, 1978.
Brochure, COBE SMS Disposable Stopcock Manifold System, 1977.
Brochure and Instructions for Use; William Harvey Model H-1500 Bubble Oxygenator; 1981; Instructions for Use; William Harvey H-530 Sampling manifold; 1980.
Brochure; Rhone-Poulenc M3 Oxygenator; translation.
Instructions for Use; M3 Oxygenator; partial translation; 1979.
Brochure, Travenol TMO Membrane Oxygenator, 1977.
Article; "Total Cardipulmonary Bypass with the Lande-Edwards Membrane Oxygenator"; *The American Journal of Cardiology*; 1972.

*Primary Examiner*—N. Bhat

[57] ABSTRACT

Blood oxyenating apparatus having a sampling access device connected to the blood outlet port and a blood inlet port of the apparatus by a sample supply line and return line and means to cause the pressure at the blood outlet port to be sufficient to cause a small continuous flow of blood through the lines and access device.

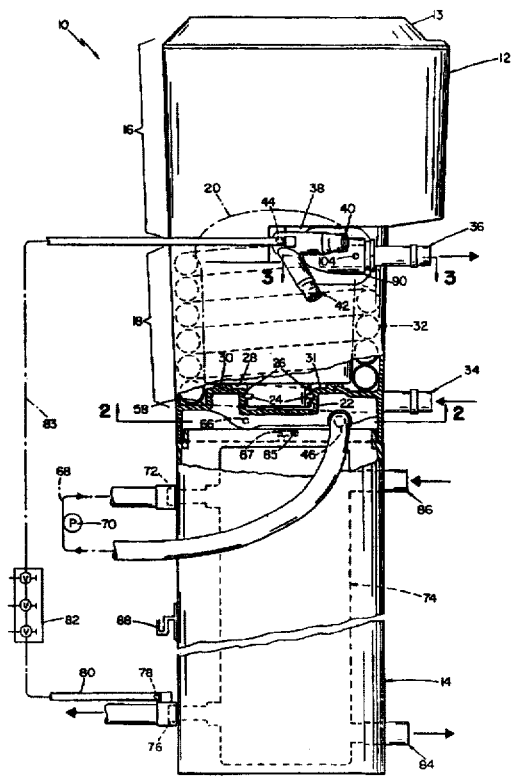

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–5 is confirmed.

New claims 6–17 are added and determined to be patentable.

6. *The apparatus of claim 5, wherein the means to remove air bubbles includes:*

*a rigid venous reservoir attached to said blood inlet port, the venous reservoir having a surface exposed to ambient air; and*

*a blood defoamer positioned within the venous reservoir to facilitate removal of bubbles introduced into the venous reservoir.*

7. *The apparatus of claim 5, wherein:*

*the means for oxygenating blood further comprises a mass transfer device including a microporous membrane positioned to separate blood flow through the transfer device from air flow through the transfer device, the microporous membrane having pores to exchange oxygen and carbon dioxide between the blood and the air flows separated by the microporous membrane; and wherein the means to remove air bubbles comprises:*

*an upper blood inflow port of the mass transfer device positioned above said blood outlet port, the upper blood inflow port and the blood outlet port communicating blood through the mass transfer device in a downward flow to increase the residence time of any air bubbles carried by the blood flow toward the blood outlet port; and*

*a higher pressure of the blood flow relative to the air flow in the mass transfer device created by the pumping means to pass air bubbles carried by the blood flow through the pores in the microporous membrane.*

8. *The apparatus of claim 7 wherein:*

*the microporous membrane defines blood flow paths within the mass transfer device to direct the blood flow against the microporous membrane and promote passage of the air bubbles through the pores in the microporous membrane.*

9. *The apparatus of claim 8, wherein the means to remove air bubbles further comprises:*

*means to inhibit downward movement of air bubbles within the blood flow paths.*

10. *The apparatus of claim 9, wherein the means to inhibit downward movement of air bubbles comprises spacer strands.*

11. *The apparatus of claim 7, wherein the means to remove air bubbles further comprises:*

*a top location within the mass transfer device to detain air bubbles which have sufficient buoyancy to inhibit the air bubbles from being carried with the downward blood flow through the mass transfer device.*

12. *The apparatus of claim 7, wherein the means to remove air bubbles further includes:*

*a rigid venous reservoir defining said blood inlet port, the venous reservoir attached to and above the mass transfer device and connected to supply blood to the blood inflow port of the mass transfer device, and the venous reservoir further having a surface exposed to ambient air.*

13. *The apparatus of claim 12, wherein the venous reservoir is integrally attached to the mass transfer device.*

14. *The apparatus of claim 12, wherein the means to remove air bubbles further includes:*

*a blood defoamer positioned within the venous reservoir to facilitate removal of bubbles introduced into the venous reservoir.*

15. *The apparatus of claim 12, wherein:*

*the pumping means is connected between the venous reservoir and the blood inflow port of the mass transfer device to deliver blood to the mass transfer device at a pressure greater than a pressure of the air flow through the mass transfer device and to return the oxygenated blood to the patient.*

16. *The apparatus of claim 15, wherein:*

*the oxygenated blood returned to the patient is substantially free of air bubbles.*

17. *The apparatus of claim 12, wherein the means to remove air bubbles further comprises:*

*a top location within the mass transfer device to detain air bubbles which have sufficient buoyancy to inhibit the air bubbles from being carried with the downward blood flow through the mass transfer device.*

* * * * *